United States Patent
Mizushima et al.

(10) Patent No.: US 11,242,332 B2
(45) Date of Patent: Feb. 8, 2022

(54) METHOD FOR PRODUCING BENZIMIDAZOLE DERIVATIVE

(71) Applicant: Sumitomo Dainippon Pharma Co., Ltd., Osaka (JP)

(72) Inventors: Shingo Mizushima, Osaka (JP); Shoukou Lee, Osaka (JP); Yoko Takahashi, Osaka (JP)

(73) Assignee: Sumitomo Dainippon Pharma Co., Ltd., Osaka (JP)

( * ) Notice: Subject to any disclaimer, the term of this patent is extended or adjusted under 35 U.S.C. 154(b) by 0 days.

(21) Appl. No.: 16/494,137

(22) PCT Filed: Mar. 14, 2018

(86) PCT No.: PCT/JP2018/009884
§ 371 (c)(1),
(2) Date: Sep. 13, 2019

(87) PCT Pub. No.: WO2018/168899
PCT Pub. Date: Sep. 20, 2018

(65) Prior Publication Data
US 2020/0071295 A1 Mar. 5, 2020

(30) Foreign Application Priority Data
Mar. 15, 2017 (JP) ............... JP2017-049458

(51) Int. Cl.
*C07D 401/12* (2006.01)
*C07D 403/12* (2006.01)
*B01J 23/44* (2006.01)
*B01J 27/045* (2006.01)
*C07D 213/64* (2006.01)

(52) U.S. Cl.
CPC ............ *C07D 401/12* (2013.01); *B01J 23/44* (2013.01); *B01J 27/045* (2013.01); *C07D 213/64* (2013.01); *C07D 403/12* (2013.01)

(58) Field of Classification Search
CPC ............. C07D 401/12; C07D 403/12
See application file for complete search history.

(56) References Cited

U.S. PATENT DOCUMENTS

| 9,688,670 B2* | 6/2017 | Komiya ............... C07D 401/04 |
| 2004/0087626 A1 | 5/2004 | Renhowe et al. |
| 2004/0122237 A1 | 6/2004 | Amiri et al. |
| 2007/0049622 A1 | 3/2007 | Dimitroff et al. |
| 2007/0161680 A1 | 7/2007 | Aikawa et al. |
| 2007/0299039 A1 | 12/2007 | Amiri et al. |
| 2008/0287682 A1 | 11/2008 | Dimitroff et al. |
| 2009/0170904 A1 | 7/2009 | Aikawa et al. |
| 2010/0196368 A1 | 8/2010 | Amiri et al. |
| 2010/0234394 A1 | 9/2010 | Aikawa et al. |
| 2010/0256375 A1 | 10/2010 | Dimitroff et al. |
| 2011/0294804 A1 | 12/2011 | Tsubio et al. |
| 2012/0277226 A1 | 11/2012 | Chen et al. |
| 2012/0288501 A1 | 11/2012 | Amiri et al. |
| 2013/0303535 A1 | 11/2013 | Tsubio et al. |
| 2013/0324579 A1 | 12/2013 | Bolli et al. |
| 2017/0107211 A1 | 4/2017 | Komiya et al. |
| 2017/0334923 A1 | 11/2017 | Kruegel et al. |
| 2018/0170881 A1 | 6/2018 | Komiya et al. |

FOREIGN PATENT DOCUMENTS

| JP | 2003-112045 | 4/2003 |
| JP | 2005-529089 | 9/2005 |
| JP | 2009-507026 | 2/2009 |
| JP | 2014-508754 | 4/2014 |
| WO | WO 2009/034433 | 3/2009 |
| WO | WO 2010/074193 | 7/2010 |
| WO | WO 2012/029636 | 3/2012 |
| WO | WO 2012/058254 | 5/2012 |
| WO | WO 2016/086158 | 6/2016 |
| WO | WO 2016/117647 | 7/2016 |
| WO | WO 2017/043636 | 3/2017 |

OTHER PUBLICATIONS

A machine generated English translation of WO 2016/117647 A1 (Sawayama et al.), 2016. (Year: 2016).*
Boydston et al., "Phase-Tunable Fluorophores Based upon Benzobis (imidazolinm) Salts," J. Aa. Chem. Soc., 2007, 129(47):14550-14551.
PCT International Preliminary Report on Patentability in International Appln. PCT/JP2018/009884, dated Sep. 17, 2019, 11 pages.

* cited by examiner

Primary Examiner — Laura L Stockton
(74) Attorney, Agent, or Firm — Fish & Richardson P.C.

(57) ABSTRACT

The present invention relates to a process to prepare a benzimidazole derivative useful as a medicament, an intermediate for preparing the medicament, and a process to prepare the intermediate.

17 Claims, No Drawings

METHOD FOR PRODUCING BENZIMIDAZOLE DERIVATIVE

TECHNICAL FIELD

The present invention relates to a process to prepare a benzimidazole derivative useful as a medicament, an intermediate for preparing the medicament, and a process to prepare the intermediate. In more detail, it relates to a benzimidazole derivative useful as a medicament for treating or preventing a disease such as neuropathic pain, an intermediate for preparing the medicament, and a process to prepare the intermediate.

BACKGROUND ART

The processes of preparing the benzimidazole derivative of the present invention and the compound having a partially-common chemical structure are disclosed in some literatures (Patent Literature 1, Patent Literature 2, Non-Patent Literature 1) However, the after-mentioned process of preparing the benzimidazole derivative of the present invention, the after-mentioned intermediate for preparing the derivative, and the after-mentioned process to prepare the intermediate are not disclosed in these literatures.

PRIOR ART

Patent Literature

[Patent Literature 1] WO 2010/074193
[Patent Literature 2] WO 2012/058254

Non-Patent Literature

[Non-Patent Literature 1] Journal of The American Chemical Society. 2007, 129, 14550-14551.

SUMMARY OF INVENTION

Technical Problem

The purpose of the present invention may be to provide a process of preparing the benzimidazole derivative (1) useful as a medicament mentioned above, said process is an industrially advantageous process which can prepare the desired product in short reaction processes without a protection/deprotection process.

Solution to Problem

The present inventors have extensively studied about processes to prepare a benzimidazole derivative of formula (1) below, their process intermediates, and processes to prepare process intermediates, and then have found that a benzimidazole derivative of formula (1) below can be effectively prepared by using a process intermediate of formula (2) below. Based upon the new findings, the present invention has been completed.

The present invention can show as follows.
(Item 1)
A process for preparing a compound of formula (1):

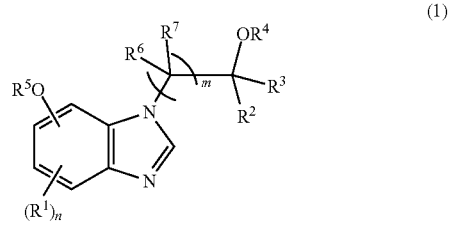

or a pharmaceutically acceptable salt thereof, wherein
$R^1$ is, independently if there are plural $R^1$, halogen, cyano, $C_{1-6}$ alkyl, or $C_{1-6}$ alkoxy, wherein the alkyl and the alkoxy may be optionally substituted with 1 to 5 the same or different halogen atoms;
n is 0, 1, 2, or 3;
$R^2$ and $R^3$ are independently hydrogen atom; $C_{1-6}$ alkyl which may be optionally substituted with 1 to 5 the same or different substituents selected from the group consisting of cyano, halogen, and hydroxy group; or $C_{3-10}$ cycloalkyl;
$R^4$ is hydrogen atom; $C_{1-6}$ alkyl which may be optionally substituted with 1 to 5 the same or different substituents selected from the group consisting of cyano, halogen, and hydroxy group; or $C_{3-10}$ cycloalkyl;
$R^5$ is $C_{6-10}$ aryl or 5- to 12-membered heteroaryl, wherein the aryl and the heteroaryl may be optionally substituted with 1 to 5 the same or different substituents selected from the group consisting of halogen atom; $C_{1-4}$ alkyl which may be optionally substituted with 1 to 5 the same or different halogen atoms; and $C_{1-4}$ alkoxy which may be optionally substituted with 1 to 5 the same or different halogen atoms;
m is 1, 2, or 3; and
$R^6$ and $R^7$ are independently (if there are plural $R^6$ or $R^7$, each $R^6$ or $R^7$ is also independently) selected from the group consisting of hydrogen atom, deuterium atom, hydroxy, $C_{1-4}$ alkyl, $C_{1-4}$ alkoxy (wherein the alkyl and the alkoxy may be optionally substituted with 1 to 5 the same or different substituents selected independently from the group consisting of halogen atom and hydroxy group), $C_{3-7}$ cycloalkyl, and $C_{3-7}$ cycloalkoxy (wherein the cycloalkyl and the cycloalkoxy may be optionally substituted with 1 to 5 the same or different substituents selected independently from the group consisting of halogen atom and hydroxy group),
comprising reducing a compound of formula (2):

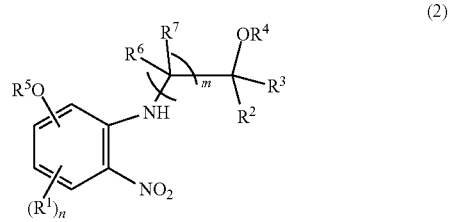

wherein $R^1$, $R^2$, $R^3$, $R^4$, $R^5$, $R^6$, $R^7$, m, and n are as defined above, and
cyclizing the reduced product with a formate equivalent.
(Item 2)
The process of Item 1, further comprising a step of preparing the compound of formula (2) which comprises reacting a compound of formula (3):

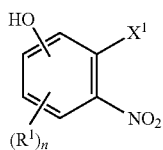
(3)

wherein R¹ and n are as defined in Item 1, X¹ is hydroxy, halogen, alkylsulfonyloxy, or arylsulfonyloxy with a compound of (4):

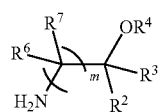
(4)

wherein R², R³, R⁴, R⁶, R⁷, and m are as defined in Item 1, and then with R⁵—X² wherein R⁵ is as defined in Item 1, and X² is halogen.

(Item 3)

The process of Item 1, further comprising a step of preparing the compound of formula (2) which comprises reacting a compound of formula (3):

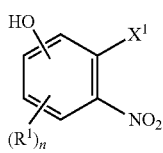
(3)

wherein R¹ and n are as defined in Item 1, X¹ is hydroxy, halogen, alkylsulfonyloxy, or arylsulfonyloxy with R⁵—X² wherein R⁵ is as defined in Item 1, and X² is halogen, and then
with a compound of (4):

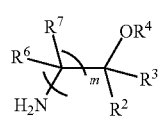
(4)

wherein R², R³, R⁴, R⁶, R⁷, and m are as defined in Item 1.

(Item 4)
A process for preparing a compound of formula (1):

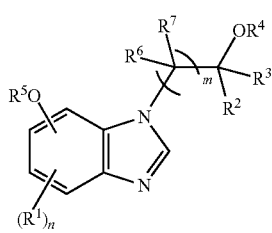
(1)

or a pharmaceutically acceptable salt thereof, wherein
R¹ is, independently if there are plural R¹, halogen, cyano, $C_{1-6}$ alkyl, or $C_{1-6}$ alkoxy, wherein the alkyl and the alkoxy may be optionally substituted with 1 to 5 the same or different halogen atoms;

n is 0, 1, 2, or 3;

R² and R³ are independently hydrogen atom; $C_{1-6}$ alkyl which may be optionally substituted with 1 to 5 the same or different substituents selected from the group consisting of cyano, halogen, and hydroxy group; or $C_{3-10}$ cycloalkyl;

R⁴ is hydrogen atom; $C_{1-6}$ alkyl which may be optionally substituted with 1 to 5 the same or different substituents selected from the group consisting of cyano, halogen, and hydroxy group; or $C_{3-10}$ cycloalkyl;

R⁵ is $C_{6-10}$ aryl or 5- to 12-membered heteroaryl, wherein the aryl and the heteroaryl may be optionally substituted with 1 to 5 the same or different substituents selected from the group consisting of halogen atoms; $C_{1-4}$ alkyl which may be optionally substituted with 1 to 5 the same or different halogen atoms; and $C_{1-4}$ alkoxy which may be optionally substituted with 1 to 5 the same or different halogen atoms;

m is 1, 2, or 3; and

R⁶ and R⁷ are independently (if there are plural R⁶ or R⁷, each R⁶ or R⁷ is also independently) selected from the group consisting of hydrogen atom, deuterium atom, hydroxy, $C_{1-4}$ alkyl, $C_{1-4}$ alkoxy (wherein the alkyl and the alkoxy may be optionally substituted with 1 to 5 the same or different substituents selected independently from the group consisting of halogen atom and hydroxy group), $C_{3-7}$ cycloalkyl, and $C_{3-7}$ cycloalkoxy (wherein the cycloalkyl and the cycloalkoxy may be optionally substituted with 1 to 5 the same or different substituents selected independently from the group consisting of halogen atom and hydroxy group), comprising the following Step A and Step B;
Step A
reacting a compound of formula (3):

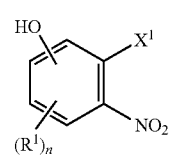
(3)

wherein R¹ and n are as defined above, X¹ is hydroxy, halogen, alkylsulfonyloxy, or arylsulfonyloxy, with a compound of (4):

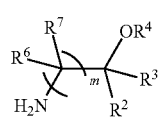

wherein $R^2$, $R^3$, $R^4$, $R^6$, $R^7$, and m are as defined above, and then with $R^5$—$X^2$ wherein $R^5$ is as defined above, and $X^2$ is halogen to prepare a compound of formula (2):

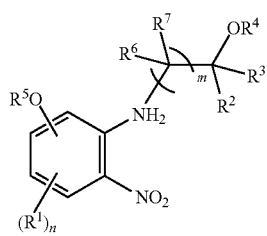

wherein $R^1$, $R^2$, $R^3$, $R^4$, $R^5$, $R^6$, $R^7$, m, and n are as defined above;

Step B reducing the compound of formula (2) and cyclizing the reduced product with a formate equivalent to prepare the compound of formula (1).

(Item 5)

A process for preparing a compound of formula (1):

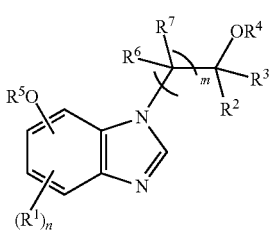

or a pharmaceutically acceptable salt thereof, wherein $R^1$ is, independently if there are plural $R^1$, halogen, cyano, $C_{1-6}$ alkyl, or $C_{1-6}$ alkoxy, wherein the alkyl and the alkoxy may be optionally substituted with 1 to 5 the same or different halogen atoms;

n is 0, 1, 2, or 3;

$R^2$ and $R^3$ are independently hydrogen atom; $C_{1-6}$ alkyl which may be optionally substituted with 1 to 5 the same or different substituents selected from the group consisting of cyano, halogen, and hydroxy group; or $C_{3-10}$ cycloalkyl;

$R^4$ is hydrogen atom; $C_{1-6}$ alkyl which may be optionally substituted with 1 to 5 the same or different substituents selected from the group consisting of cyano, halogen, and hydroxy group; or $C_{3-10}$ cycloalkyl;

$R^5$ is $C_{6-10}$ aryl or 5- to 12-membered heteroaryl, wherein the aryl and the heteroaryl may be optionally substituted with 1 to 5 the same or different substituents selected from the group consisting of halogen atoms; $C_{1-4}$ alkyl which may be optionally substituted with 1 to 5 the same or different halogen atoms; and $C_{1-4}$ alkoxy which may be optionally substituted with 1 to 5 the same or different halogen atoms;

m is 1, 2, or 3; and $R^6$ and $R^7$ are independently (if there are plural $R^6$ or $R^7$, each $R^6$ or $R^7$ is also independently) selected from the group consisting of hydrogen atom, deuterium atom, hydroxy, $C_{1-4}$ alkyl, $C_{1-4}$ alkoxy (wherein the alkyl and the alkoxy may be optionally substituted with 1 to 5 the same or different substituents selected independently from the group consisting of halogen atom and hydroxy group), $C_{3-7}$ cycloalkyl, and $C_{3-7}$ cycloalkoxy (wherein the cycloalkyl and the cycloalkoxy may be optionally substituted with 1 to 5 the same or different substituents selected independently from the group consisting of halogen atom and hydroxy group), comprising the following Step C, Step D, and Step E;

Step C reacting a compound of formula (3):

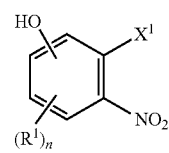

wherein $R^1$ and n are as defined above, $X^1$ is hydroxy, halogen, alkylsulfonyloxy, or arylsulfonyloxy, with a compound of (4):

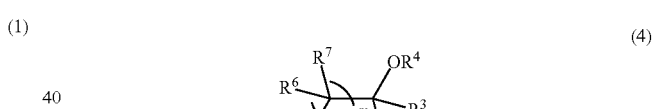

wherein $R^2$, $R^3$, $R^4$, $R^6$, $R^7$, and m are as defined above to prepare a compound of formula (5):

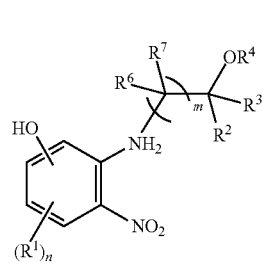

wherein $R^1$, $R^2$, $R^3$, $R^4$, $R^5$, $R^6$, $R^7$, m, and n are as defined above;

Step D reducing the compound of formula (5) and cyclizing the reduced product with a formate equivalent to prepare the compound of formula (6):

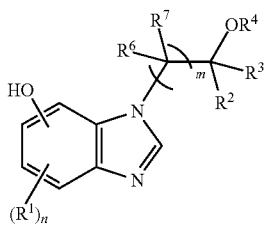

(6)

wherein $R^1$, $R^2$, $R^3$, $R^4$, $R^5$, $R^6$, $R^7$, m, and n are as defined above;

Step E reacting the compound of formula (6) with $R^5$—$X^2$ wherein $R^5$ is as defined above, and $X^2$ is halogen to prepare a compound of formula (1).

(Item 6)

The process of any one of Items 1 to 5, wherein the compound of formula (1) is a compound of formula (1'):

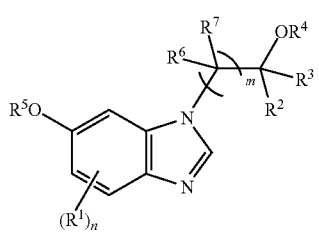

(1')

wherein $R^1$, $R^2$, $R^3$, $R^4$, $R^5$, $R^6$, $R^7$, m, and n are as defined in Item 1.

(Item 7)

The process of any one of Items 2 to 6, wherein
n is 0;
$R^2$ and $R^3$ are independently hydrogen atom or $C_{1-6}$ alkyl;
$R^4$ is hydrogen atom or $C_{1-6}$ alkyl;
$R^5$ is phenyl, or 5- or 6-membered heteroaryl, wherein the phenyl and the heteroaryl may be optionally substituted with 1 to 5 the same or different substituents selected from the group consisting of halogen; $C_{1-4}$ alkyl which may be optionally substituted with 1 to 5 the same or different halogen atoms; and $C_{1-4}$ alkoxy which may be optionally substituted with 1 to 5 the same or different halogen atoms;
m is 1;
$R^6$ and $R^7$ are independently hydrogen atom, deuterium atom, or $C_{1-4}$ alkyl;
$X^1$ is halogen; and
$X^2$ is fluorine atom or bromine atom.

(Item 8)

The process of any one of Items 2 to 7, wherein
$R^2$ and $R^3$ are $C_{1-4}$ alkyl;
$R^4$, $R^6$ and $R^7$ are hydrogen atom; and
$X^1$ and $X^2$ are fluorine atom.

(Item 9)

The process of any one of Items 1 to 8, wherein
$R^5$ is pyridyl, pyrazinyl, pyrimidinyl, or pyridazinyl, wherein the pyridyl, the pyrazinyl, the pyrimidinyl, and the pyridazinyl may be optionally substituted with 1 to 5 the same or different substituents selected from the group consisting of halogen; $C_{1-4}$ alkyl which may be optionally substituted with 1 to 5 the same or different halogen atoms; and $C_{1-4}$ alkoxy which may be optionally substituted with 1 to 5 the same or different halogen atoms.

(Item 10)

The process of any one of Items 1 to 8, wherein
$R^5$ is formula (7):

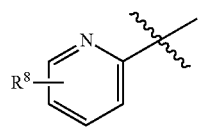

(7)

wherein $R^8$ is halogen; $C_{1-4}$ alkyl which may be optionally substituted with 1 to 5 the same or different halogen atoms; or $C_{1-4}$ alkoxy which may be optionally substituted with 1 to 5 the same or different halogen atoms.

(Item 11)

The process of any one of Items 1 to 10, wherein the reduction reaction is carried out with a reducing metal, a reducing metal salt, or a mixture of a reducing metal and a reducing metal salt.

(Item 12)

The process of any one of Items 1 to 10, wherein the reduction reaction is carried out with a reducing metal.

(Item 13)

The process of Item 12, wherein the reducing metal is zinc or iron.

(Item 14)

The process of any one of Items 11 to 13, wherein an oxide-layer remover is also used in the reduction reaction.

(Item 15)

The process of Item 14, wherein the oxide-layer remover is lithium bromide, lithium chloride, or chlorotrimethylsilane.

(Item 16)

The process of any one of Items 1 to 10, wherein the reduction reaction is carried out with a catalyst for catalytic reduction under hydrogen atmosphere.

(Item 17)

The process of Item 16, wherein the catalyst for catalytic reduction is palladium-carbon or platinum sulfide on carbon.

(Item 18)

The process of any one of Items 1 to 17, wherein the reduction reaction is carried out in the presence of an acid.

(Item 19)

The process of any one of Items 1 to 18, wherein the cyclization reaction is carried out in the presence of an acid.

(Item 20)

The process of any one of Items 1 to 19, wherein the formate equivalent is one or more selected from the group consisting of orthoformate triester (e.g. trimethyl orthoformate, triethyl orthoformate), formic acid ester (e.g. methyl formate, ethyl formate), and formate (e.g. zinc formate, sodium formate, ammonium formate).

(Item 21)

The process of Item 20, wherein the formate equivalent is orthoformate triester.

(Item 22)

The process of any one of Items 1 to 21, wherein the reduction and the cyclization are carried out in one-pot reaction.

(Item 23)

The process of any one of Items 1 to 21, wherein in the reduction and the cyclization, the nitro is reduced, followed by adding an acid and a formate equivalent to make cyclization.

(Item 24)

The process of any one of Items 1 to 22, wherein in the reduction and the cyclization, the nitro is reduced in the presence of an acid and a formate equivalent to make cyclization in the reaction system after the reduction.

(Item 25)

The process of any one of Items 1 to 24, wherein the acid is formic acid.

(Item 26)

A compound of formula (8):

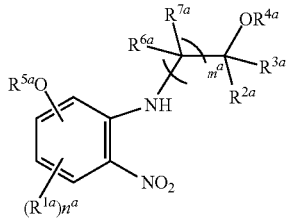

(8)

or a salt thereof, wherein $R^{1a}$ is, independently if there are plural $R^{1a}$, halogen, cyano, $C_{1-6}$ alkyl, or $C_{1-6}$ alkoxy, wherein the alkyl and the alkoxy may be optionally substituted with 1 to 5 the same or different halogen atoms;

$n^a$ is 0, 1, 2, or 3;

$R^{2a}$ and $R^{3a}$ are independently hydrogen atom, $C_{1-6}$ alkyl which may be optionally substituted with 1 to 5 the same or different substituents selected from the group consisting of cyano, halogen, and hydroxy group; or $C_{3-10}$ cycloalkyl;

$R^{4a}$ is hydrogen atom;

$R^{5a}$ is formula (9):

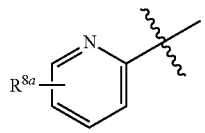

(9)

wherein $R^{8a}$ is halogen; $C_{1-4}$ alkyl which may be optionally substituted with 1 to 5 the same or different halogen atoms; or $C_{1-4}$ alkoxy which may be optionally substituted with 1 to 5 the same or different halogen atoms;

$m^a$ is 1, 2, or 3; and $R^{6a}$ and $R^{7a}$ are independently (if there are plural $R^{6a}$ or $R^{7a}$, each $R^{6a}$ or $R^{7a}$ is also independently) hydrogen atom, deuterium atom, hydroxy, $C_{1-4}$ alkyl, $C_{1-4}$ alkoxy (wherein the alkyl and the alkoxy may be optionally substituted with 1 to 5 the same or different substituents selected independently from the group consisting of halogen atom and hydroxy group), $C_{3-7}$ cycloalkyl, or $C_{3-7}$ cycloalkoxy (wherein the cycloalkyl and the cycloalkoxy may be optionally substituted with 1 to 5 the same or different substituents selected independently from the group consisting of halogen atom and hydroxy group)

(Item 27)

The compound of Item 26 or a salt thereof, wherein $R^{1a}$ is, independently if there are plural $R^{1a}$, halogen, $C_{1-6}$ alkyl, or $C_{1-6}$ alkoxy, wherein the alkyl and the alkoxy may be optionally substituted with 1 to 5 fluorine atoms;

$n^a$ is 0, 1, 2, or 3;

$R^{2a}$ and $R^{3a}$ are independently hydrogen atom, or $C_{1-6}$ alkyl which may be optionally substituted with 1 to 5 fluorine atoms;

$R^{4a}$ is hydrogen atom;

$m^a$ is 1; and $R^{6a}$ and $R^{7a}$ are independently hydrogen atom, deuterium atom, or $C_{1-4}$ alkyl which may be optionally substituted with 1 to 5 fluorine atoms.

(Item 28)

The compound of Item 26 or 27, or a salt thereof, wherein the compound of formula (8) is a compound of formula (8'):

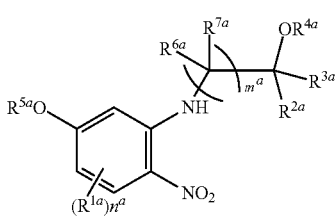

(8')

wherein $R^{1a}$, $R^{2a}$, $R^{3a}$, $R^{4a}$, $R^{5a}$, $R^{6a}$, $R^{7a}$, $m^a$, and $n^a$ are as defined above.

Effect of the Invention

The present invention has made it possible to provide a process of preparing a benzimidazole derivative, said process can prepare the desired product in short reaction processes without a protection/deprotection process. In a preferred embodiment of the present invention, besides the above-mentioned advantage, the present invention provides a process of preparing a benzimidazole derivative, said process is an industrially advantageous process which can prepare the desired product having high purity in high yield via a simple process without the purification by column chromatography.

DESCRIPTION OF EMBODIMENTS

Hereinafter, each term used herein is explained in detail.

The "halogen" includes fluorine, chlorine, bromine, and iodine.

The "$C_{1-4}$ alkyl" means a straight or branched chain alkyl having 1 to 4 carbon atoms, and the "$C_{1-6}$ alkyl" means a straight or branched chain alkyl having 1 to 6 carbon atoms. The "$C_{1-3}$ alkyl" includes, for example, methyl, ethyl, propyl, and isopropyl. The "$C_{1-4}$ alkyl" includes, for example, butyl, isobutyl, sec-butyl, and tert-butyl, besides the examples of the above "$C_{1-3}$ alkyl". The "$C_{1-6}$ alkyl" includes, for example, pentyl, isopentyl, neopentyl, 1-ethylpropyl, and hexyl, besides the examples of the above "$C_{1-4}$ alkyl". The "$C_{1-6}$ alkyl" includes, preferably "$C_{1-4}$ alkyl", more preferably "$C_{1-3}$ alkyl", even more preferably methyl and ethyl.

The "$C_{1-6}$ alkoxy" means oxy group substituted with the above "$C_{1-6}$ alkyl". The "$C_{1-3}$ alkoxy" includes, for example, methoxy, ethoxy, propoxy, and 1-methylethoxy. The "$C_{1-4}$ alkoxy" includes, for example, butoxy, 1-methylpropoxy, 2-methylpropoxy, and 1,1-dimethylethoxy, besides the examples of the above "$C_{1-3}$ alkoxy". The "$C_{1-6}$ alkoxy" includes, for example, pentyloxy and hexyloxy, besides the examples of the above "$C_{1-4}$ alkoxy". The "$C_{1-6}$ alkoxy" includes, preferably "$C_{1-4}$ alkoxy", more preferably "$C_{1-3}$ alkoxy", even more preferably methoxy and ethoxy.

The "$C_{3-10}$ cycloalkyl" means a non-aromatic cyclic hydrocarbon group (i.e., saturated hydrocarbon group and partially-unsaturated hydrocarbon group) having 3 to 10 carbon atoms, which includes a partially-bridged structure thereof. The "$C_{3-6}$ cycloalkyl" includes, for example, cyclopropyl, cyclobutyl, cyclopentyl, cyclohexyl, cyclopentenyl, and cyclohexenyl. The "$C_{3-7}$ cycloalkyl" includes, for example, cycloheptyl and cycloheptenyl, besides the examples of the above "$C_{3-6}$ cycloalkyl". The "$C_{3-10}$ cycloalkyl" includes, for example, cyclooctyl, cyclononanyl, cyclodecanyl, and adamantyl, besides the examples of the above "$C_{3-7}$ cycloalkyl". The "$C_{3-10}$ cycloalkyl" includes, preferably "$C_{3-7}$ cycloalkyl", more preferably "$C_{3-6}$cycloalkyl", even more preferably cyclopropyl, cyclobutyl, cyclopentyl and cyclohexyl.

The "$C_{3-7}$ cycloalkoxy" means oxy group substituted with the above "$C_{3-7}$ cycloalkyl". The "$C_{3-6}$ cycloalkoxy" includes, for example, cyclopropyloxy, cyclobutyloxy, cyclopentyloxy, and cyclohexyloxy. The "$C_{3-7}$ cycloalkoxy" includes, for example, cycloheptyloxy, besides the examples of the above "$C_{3-6}$ cycloalkoxy". The "$C_{3-7}$ cycloalkoxy" includes, preferably "$C_{3-6}$ cycloalkoxy", more preferably cyclopropyloxy, cyclobutyloxy, cyclopentyloxy, and cyclohexyloxy, the most preferably cyclohexyloxy.

The "$C_{6-10}$ aryl" used herein means aromatic hydrocarbon group having 6-10 carbon atoms. The "$C_{6-10}$ aryl" includes, for example, phenyl, 1-naphthyl, and 2-naphthyl. Preferably, it is phenyl.

The "5- to 12-membered heteroaryl" means a mono- or bi-cyclic aromatic heterocyclyl group (mono-cyclic heteroaryl or bi-cyclic heteroaryl) composed of 5 to 12 atoms having 1 to 4 heteroatoms selected from the group consisting of nitrogen atom, oxygen atom, and sulfur atom, which includes preferably 5- or 6-membered heteroaryl, more specifically 5- or 6-membered nitrogen-containing heteroaryl. The bi-cyclic heteroaryl means a condensed ring in which two the same or different mono-cyclic heteroaryls are fused, a mono-cyclic heteroaryl and an aromatic ring (for example, benzene) are fused, or a mono-cyclic heteroaryl and a non-aromatic ring (for example, cyclohexane, piperidine) are fused. The "5- or 6-membered nitrogen-containing heteroaryl" means a mono-cyclic aromatic heterocyclyl group composed of 5 to 6 atoms having 1 to 3 nitrogen atoms, which includes, for example, pyridyl, pyridazinyl, isothiazolyl, pyrrolyl, thiazolyl, imidazolyl, pyrimidinyl, thiadiazolyl, pyrazolyl, oxazolyl, isoxazolyl, pyrazinyl, triazinyl, triazolyl, imidazolidinyl, oxadiazolyl, and tetrazolyl. The "5- or 6-membered heteroaryl" includes, for example, furyl and thienyl, besides the examples of the above "5- or 6-membered nitrogen-containing heteroaryl". The "5- to 12-membered heteroaryl" includes, for example, indolyl, indazolyl, quinolyl, isoquinolyl, benzofuranyl, benzothienyl, benzoxazolyl, benzothiazolyl, benzisoxazolyl, benzisothiazolyl, benzotriazolyl, benzimidazolyl, and 6,11-dihydrodibenzo[b,e]thiepinyl group, besides the examples of the above "5- or 6-membered heteroaryl". The "5- to 12-membered heteroaryl" includes, preferably "5- or 6-membered heteroaryl", more preferably "5- or 6-membered nitrogen-containing heteroaryl", even more preferably pyrazolyl, imidazolyl, pyridyl, pyrimidinyl, pyrazinyl, and pyridazinyl, particularly preferably pyridyl.

The "alkylsulfonyloxy" means sulfonyloxy group substituted with the above "$C_{1-4}$ alkyl" which may be optionally substituted with 1 to 5 the same or different halogen atoms. The "alkylsulfonyloxy" includes, for example, methanesulfonyloxy and trifluoromethanesulfonyloxy.

The "arylsulfonyloxy" means sulfonyloxy group substituted with the above "$C_{6-10}$ aryl" which may be optionally substituted with $C_{1-4}$ alkyl. The "arylsulfonyloxy" includes, for example, para-toluenesulfonyloxy.

The "reducing metal, reducing metal salt, or mixture of a reducing metal and a reducing metal salt" means a metal or a metal salt which can undergo reduction reaction by emitting an electron, or a mixture thereof. The "reducing metal" includes, for example, zinc, iron, tin, and titanium. The "reducing metal salt" includes, for example, ferric chloride, tin chloride, and titanium chloride. The "reducing metal, reducing metal salt, or mixture of a reducing metal and a reducing metal salt" includes, preferably zinc or iron.

The "catalyst for catalytic reduction" is a metal dispersed/loaded on a carrier such as carbon, which means a catalyst for reducing an unsaturated bond, a nitro, etc. under hydrogen atmosphere. The "catalyst for catalytic reduction" includes, for example, palladium catalysts such as palladium-carbon and palladium hydroxide-carbon; nickel catalysts such as Raney nickel; cobalt catalysts; platinum catalysts such as platinum sulfide on carbon; ruthenium catalysts; and rhodium catalysts. The "catalyst for catalytic reduction" includes, preferably palladium catalysts and platinum catalysts; more preferably palladium-carbon and platinum sulfide on carbon.

The "formate equivalent" means a compound which can undergo a similar chemical conversion to formic acid in organic synthetic chemistry. The "formate equivalent" includes, for example, an orthoformate triester such as trimethyl orthoformate and triethyl orthoformate; a formic acid ester such as methyl formate and ethyl formate; and a formate such as zinc formate, sodium formate, and ammonium formate. The "formate equivalent" includes, preferably an orthoformate, more preferably trimethyl orthoformate and triethyl orthoformate, even more preferably trimethyl orthoformate.

The "acid" which may be used in the reduction and/or the cyclization means a substance which ionizes to produce hydrogen ion when the substance is dissolved in water. The "acid" includes, for example, an inorganic acid such as hydrochloric acid, sulfuric acid, and nitric acid; and an organic acid such as formic acid, acetic acid, and butyric acid. The "acid" includes, preferably hydrochloric acid, formic acid, and acetic acid; more preferably hydrochloric acid and formic acid; even more preferably formic acid.

The reduction and cyclization steps of a compound of formula (2) may be carried out in order of reduction step and then cyclization step, or the both reactions may be carried out in one-pot.

The "one-pot reaction" means a synthetic technique to carry out multistep reactions by throwing reactants in order into a reaction vessel. The "one-pot reaction" does not require isolation/purification in each step, thus it is expected to reduce a number of waste materials such as solvents, reaction time, and labor effort. In addition, one-pot reaction can bring in an economical merit such as greatly-simplified process, as well as a reduction in environment load since one-pot reaction requires only one reaction vessel.

The "an oxide-layer remover" means a compound which can remove an oxide on the surface of a metal such as iron and zinc to enhance the activity suitably. The "an oxide-layer remover" includes, for example, a lithium salt such as lithium chloride and lithium bromide; an inorganic acid such as hydrochloric acid and sulfuric acid; an organic acid such as formic acid and acetic acid; a dihalogenated hydrocarbon such as 1,2-diiodoethane and 1,2-dibromoethane; and a halogenated silane such as chlorotrimethylsilane and dichlorodimethylsilane. The "an oxide-layer remover" includes, preferably formic acid, lithium chloride and lithium bromide, more preferably lithium chloride and lithium bromide, even more preferably lithium bromide.

The "make cyclization in the reaction system after the reduction" means that the precursor for cyclization which is obtained by reducing the nitro group in the reduction reaction is used in the cyclization reaction with an acid and a formate equivalent, without isolating the precursor.

Preferred embodiments of the present invention are in detail shown below.

$R^1$ includes preferably halogen; more preferably fluorine atom and chlorine atom.

n includes preferably 0, 1, and 2; more preferably 0 and 1; even more preferably 0.

$R^2$ and $R^3$ includes preferably hydrogen atom and $C_{1-6}$ alkyl; more preferably hydrogen atom and $C_{1-4}$ alkyl; even more preferably $C_{1-3}$ alkyl; particularly preferably methyl and ethyl; the most preferably methyl.

$R^4$ includes preferably hydrogen atom and $C_{1-6}$ alkyl; more preferably hydrogen atom and $C_{1-3}$ alkyl; even more preferably hydrogen atom, methyl, and ethyl, the most preferably hydrogen atom.

$R^5$ includes preferably $C_{6-10}$ aryl and 5- or 6-membered heteroaryl (wherein the aryl and the heteroaryl may be optionally substituted with 1 to 5 the same or different substituents selected from the group consisting of halogen atom; $C_{1-4}$ alkyl which may be optionally substituted with 1 to 5 fluorine atoms; and $C_{1-4}$ alkoxy which may be optionally substituted with 1 to 5 fluorine atoms); more preferably phenyl and 5- or 6-membered nitrogen-containing heteroaryl (wherein the phenyl and the heteroaryl may be optionally substituted with 1 to 5 the same or different substituents selected from the group consisting of halogen; $C_{1-4}$ alkyl which may be optionally substituted with 1 to 5 fluorine atoms; $C_{1-4}$ alkoxy which may be optionally substituted with 1 to 5 fluorine atoms); even more preferably phenyl and 6-membered heteroaryl (wherein the phenyl and the heteroaryl may be optionally substituted with 1 to 5 the same or different substituents selected from the group consisting of halogen; $C_{1-4}$ alkyl which may be optionally substituted with 1 to 5 fluorine atoms; and alkoxy which may be optionally substituted with 1 to 5 fluorine atoms); particularly preferably pyridyl optionally-substituted with $C_{1-4}$ alkyl which may be optionally substituted with 1 to 5 fluorine atoms; the most preferably pyridyl which may be optionally substituted with trifluoromethyl.

m includes preferably 1 and 2; more preferably 1.

$R^6$ and $R^7$ include preferably hydrogen atom, deuterium atom, hydroxy group, $C_{1-4}$ alkyl which may be optionally substituted with 1 to 5 the same or different halogen atoms, and $C_{3-7}$ cycloalkyl which may be optionally substituted with 1 to 5 the same or different halogen atoms; more preferably hydrogen atom, deuterium atom, $C_{1-4}$ alkyl, and $C_{3-7}$ cycloalkyl; even more preferably hydrogen atom, and deuterium atom; particularly preferably hydrogen atom.

$R^8$ includes preferably halogen, $C_{1-4}$ alkyl which may be optionally substituted with 1 to 5 fluorine atoms, and $C_{1-4}$ alkoxy which may be optionally substituted with 1 to 5 fluorine atoms; more preferably fluorine atom, chlorine atom, $C_{1-4}$ alkyl which may be optionally substituted with 1 to 5 fluorine atoms, and $C_{1-4}$ alkoxy which may be optionally substituted with 1 to 5 fluorine atoms; even more preferably fluorine atom, chlorine atom, and $C_{1-3}$ alkyl which may be optionally substituted with 1 to 5 fluorine atoms; even more preferably $C_{1-3}$ alkyl which may be optionally substituted with 1 to 5 fluorine atoms; particularly preferably trifluoromethyl.

$X^1$ includes preferably halogen, alkylsulfonyloxy, and arylsulfonyloxy; more preferably halogen; even more preferably fluorine atom and chlorine atom; particularly preferably fluorine atom.

$X^2$ includes preferably fluorine atom and bromine atom; more preferably fluorine atom.

$R^{1a}$ includes preferably halogen; more preferably fluorine atom and chlorine atom.

$n^a$ includes 0, 1, and 2; more preferably 0 and 1; even more preferably 0.

$R^{2a}$ and $R^{3a}$ include preferably hydrogen atom and $C_{1-6}$ alkyl; more preferably hydrogen atom and $C_{1-4}$ alkyl; even more preferably $C_{1-3}$ alkyl; particularly preferably methyl and ethyl; the most preferably methyl.

$m^a$ includes preferably 1 and 2; more preferably 1.

$R^{6a}$ and $R^{7a}$ include preferably hydrogen atom, deuterium atom, hydroxy group, $C_{1-4}$ alkyl which may be optionally substituted with 1 to 5 the same or different halogen atoms, and $C_{3-7}$ cycloalkyl which may be optionally substituted with 1 to 5 the same or different halogen atoms; more preferably hydrogen atom, deuterium atom, $C_{1-4}$ alkyl, and $C_{3-7}$ cycloalkyl; even more preferably hydrogen atom and deuterium atom; particularly preferably hydrogen atom.

$R^{8a}$ includes preferably halogen, $C_{1-4}$ alkyl which may be optionally substituted with 1 to 5 fluorine atoms, and $C_{1-4}$ alkoxy which may be optionally substituted with 1 to 5 fluorine atoms; more preferably fluorine atom, chlorine atom, $C_{1-4}$ alkyl which may be optionally substituted with 1 to 5 fluorine atoms, and $C_{1-4}$ alkoxy which may be optionally substituted with 1 to 5 fluorine atoms; even more preferably fluorine atom, chlorine atom, and $C_{1-3}$ alkyl which may be optionally substituted with 1 to 5 fluorine atoms; even more preferably $C_{1-3}$ alkyl which may be optionally substituted with 1 to 5 fluorine atoms; particularly preferably trifluoromethyl.

One embodiment of the compound of formula (1) includes (A). (A) The compound or a pharmaceutically acceptable salt thereof, wherein
n is 0, 1, or 2;
$R^1$ is, independently if there are plural $R^1$, halogen or $C_{1-6}$ alkyl which may be optionally substituted with 1 to 5 the same or different halogen atoms;
$R^2$ and $R^3$ are independently $C_{1-6}$ alkyl;
$R^4$ is hydrogen atom;
m is 1;
$R^5$ is 6-membered heteroaryl which may be optionally substituted with 1 to 5 the same or different substituents selected from the group consisting of halogen, $C_{1-4}$ alkyl which may be optionally substituted with 1 to 5 the same or different halogen atoms, and $C_{1-4}$ alkoxy which may be optionally substituted with 1 to 5 the same or different halogen atoms; and
$R^6$ and $R^7$ are independently hydrogen atom, deuterium atom, or $C_{1-4}$ alkyl.

One embodiment of the compound of formula (1) includes (A'). (A') The compound of formula (1') or a pharmaceutically acceptable salt thereof, wherein $R^1$, $R^2$, $R^3$, $R^4$, $R^5$, $R^6$, $R^7$, m, and n are as defined in the above (A).

One embodiment of the compound of formula (1) includes (B). (B) The compound or a pharmaceutically acceptable salt thereof, wherein n is 0;

$R^2$ and $R^3$ are independently $C_{1-6}$ alkyl;

$R^4$ is hydrogen atom;

m is 1;

$R^5$ is pyridyl (which may be optionally substituted with 1 to 5 the same or different substituents selected from the group consisting of halogen, $C_{1-4}$ alkyl which may be optionally substituted with 1 to 5 the same or different halogen atoms, and $C_{1-4}$ alkoxy which may be optionally substituted with 1 to 5 the same or different halogen atoms); and $R^6$ and $R^7$ are independently hydrogen atom, deuterium atom, or $C_{1-4}$ alkyl.

One embodiment of the compound of formula (1) includes (B'). (B') The compound of formula (1') or a pharmaceutically acceptable salt thereof, wherein $R^2$, $R^3$, $R^4$, $R^5$, $R^6$, $R^7$, m, and n are as defined in the above (B).

One embodiment of the compound of formula (8) includes (a). (a) The compound or a pharmaceutically acceptable salt thereof, wherein $n^a$ is 0, 1, or 2;

$R^{1a}$ is, independently if there are plural $R^{1a}$, halogen or $C_{1-6}$ alkyl which may be optionally substituted with 1 to 5 the same or different halogen atoms;

$R^{2a}$ and $R^{3a}$ are independently $C_{1-6}$ alkyl;

$R^{4a}$ is hydrogen atom;

$m^a$ is 1;

$R^{5a}$ is formula (9);

$R^{6a}$ and $R^{7a}$ are independently hydrogen atom, deuterium atom, or $C_{1-4}$ alkyl; and $R^{8a}$ is halogen; $C_{1-4}$ alkyl which may be optionally substituted with 1 to 5 the same or different halogen atoms; or $C_{1-4}$ alkoxy which may be optionally substituted with 1 to 5 the same or different halogen atoms.

One embodiment of the compound of formula (8) includes (a'). (a') The compound of formula (8') or a pharmaceutically acceptable salt thereof, wherein $R^{1a}$, $R^{2a}$, $R^{3a}$, $R^{4a}$, $R^{5a}$, $R^{6a}$, $R^{7a}$, $R^{8a}$, $m^a$, and $n^a$ are as defined in the above (a).

One embodiment of the compound of formula (8) includes (b). (b) The compound or a pharmaceutically acceptable salt thereof, wherein $n^a$ is 0;

$R^{2a}$ and $R^{3a}$ are independently $C_{1-6}$ alkyl;

$R^{4a}$ is hydrogen atom;

$m^a$ is 1;

$R^{5a}$ is formula (9);

$R^{6a}$ and $R^{7a}$ are independently hydrogen atom, deuterium atom, or $C_{1-4}$ alkyl; and $R^{8a}$ is $C_{1-4}$ alkyl which may be optionally substituted with 1 to 5 fluorine atoms, or $C_{1-4}$ alkoxy which may be optionally substituted with 1 to 5 fluorine atoms.

One embodiment of the compound of formula (8) includes (b'). (b') The compound of formula (8') or a pharmaceutically acceptable salt thereof, wherein $R^{2a}$, $R^{3a}$, $R^{4a}$, $R^{5a}$, $R^{6a}$, $R^{7a}$, $R^{8a}$, $m^a$, and $n^a$ are as defined in the above (b).

The "pharmaceutically acceptable salt" includes an acid addition salt and a base addition salt. The acid addition salt includes, for example, inorganic acid salts such as hydrochloride, hydrobromide, sulfate, hydroiodide, nitrate, and phosphate; and organic acid salts such as citrate, oxalate, phthalate, fumarate, maleate, succinate, malate, acetate, formate, propionate, benzoate, trifluoroacetate, methanesulfonate, benzenesulfonate, para-toluenesulfonate, and camphorsulfonate. The base addition salt includes, for example, inorganic basic salts such as sodium salt, potassium salt, calcium salt, magnesium salt, barium salt, and aluminium salt; and salts with organic base such as trimethylamine, triethylamine, pyridine, picoline, 2,6-lutidine, ethanolamine, diethanolamine, triethanolamine, tromethamine [tris(hydroxymethyl)methylamine], tert-butylamine, cyclohexylamine, dicyclohexylamine, and N,N-dibenzylethylamine. In addition, the "pharmaceutically acceptable salt" also includes salts with basic amino acid or acidic amino acid such as arginine, lysine, ornithine, aspartate, and glutamate.

The starting materials and intermediates used herein may be salts thereof. Salts of the starting materials and intermediates are preferably conventional non-toxic salts. The salts include acid-addition salts such as organic acid salts (e.g. acetate, trifluoroacetate, maleate, fumarate, citrate, tartrate, methanesulfonate, benzenesulfonate, formate, para-toluenesulfonate, etc.) and inorganic acid salts (e.g. hydrochloride, hydrobromide, hydroiodide, sulfate, nitrate, phosphate, etc.); salts with amino acid (e.g. arginine, aspartate, glutamate, etc.); metal salts such as alkali metal salts (e.g. sodium salt, potassium salt, etc.) and alkaline earth metal salts (e.g. calcium salt, magnesium salt, etc.); ammonium salts; and organic basic salts (e.g. trimethylamine salt, triethylamine salt, pyridine salt, picoline salt, dicyclohexyl amine salt, N,N'-dibenzylethylenediamine salt, etc.), which may be suitably selected by a skilled person.

Processes to prepare the compounds of the present invention are mentioned below. The starting materials that are not described in the explanation below are commercially available, or can be prepared in a known manner or in a similar manner to a known one.

Process 1:

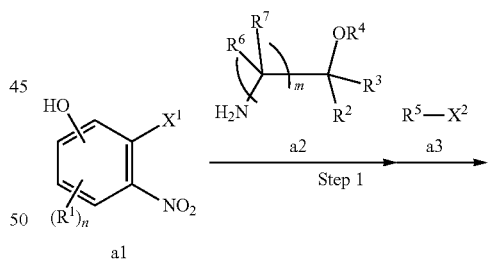

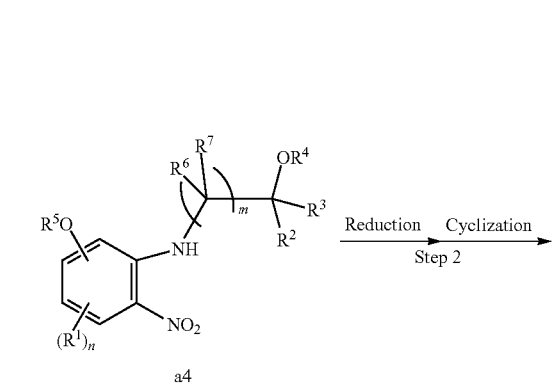

-continued

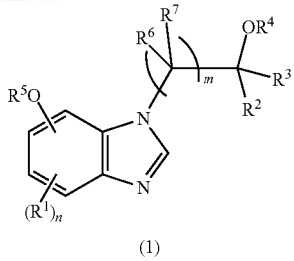

(1)

In the above scheme, $R^1$, $R^2$, $R^3$, $R^4$, $R^5$, $R^6$, $R^7$, m, and n are as defined in Item 1, and $X^1$, $X^2$ are as defined in Item 2.

Step 1:

Compound a4 can be prepared by reacting Compound a1 and Compound a2 in the presence or absence of a suitable base in a suitable solvent, and then reacting the product with Compound a3. The step can be also carried out in one-pot reaction. In addition, it is possible to reverse the reaction-order of each compound, i.e., Compound a4 can be also prepared by reacting Compound a1 and Compound a3, and then reacting the product with Compound a2.

The base used herein includes inorganic bases such as sodium bicarbonate, sodium hydroxide, potassium hydroxide, potassium carbonate, and cesium carbonate; and organic bases such as triethylamine, diisopropylethylamine, and DABCO (1,4-diazabicyclo[2.2.2]octane); preferably diisopropylethylamine, sodium bicarbonate, potassium carbonate, and cesium carbonate. When an excessive amount of Compound a2 is used, the reaction does not necessarily require the use of a base.

The solvent used herein includes ether solvents such as tetrahydrofuran, dimethoxyethane, and 1,4-dioxane, N,N-dimethylformamide, N-methylpyrrolidone, and acetonitrile; preferably N-methylpyrrolidone.

The reaction time is generally 10 minutes to 30 hours, preferably 2 hours to 25 hours, for each step, the reaction of Compound a1 and Compound a2, and the subsequent reaction with Compound a3.

The reaction temperature is generally 0° C. to boiling point of a solvent used herein, preferably 60° C. to 130° C., for each step, the reaction of Compound a1 and Compound a2, and the subsequent reaction with Compound a3.

Step 2:

Compound (1) can be prepared by reducing the nitro group of Compound a4 under a suitable reduction condition in a suitable solvent and then cyclizing the product with formic acid or a formate equivalent in the presence of a suitable catalyst in a suitable solvent. The step can be also carried out in one-pot reaction. In addition, the cyclization of the present step can be also carried out after isolating the phenylenediamine compound (precursor for cyclization) that is obtained by the reduction of the nitro group.

The reduction condition used herein includes nitro-reduction conditions which are broadly used in organic synthetic reaction, for example, catalytic reduction with palladium-carbon, sulfur-poisoning platinum-carbon, etc. under hydrogen atmosphere; metal reduction with zinc, iron, tin, etc.; hydride reduction with lithium aluminum hydride, etc. When a metal reduction with zinc is used as the reduction condition, it is preferable to use an oxide-layer remover (such as lithium bromide, lithium chloride, and chlorotrimethylsilane) with the metal. And, zinc used herein may be pretreated before the reaction by washing its surface with diluted hydrochloric acid or acetic acid and drying the washed zinc.

The solvent used in the reduction reaction includes general solvents used in each reduction condition. In case of catalytic reduction, the solvent includes, for example, methanol, ethanol, tetrahydrofuran, and ethyl acetate. In case of metal reduction, the solvent includes, for example, tetrahydrofuran, acetic acid, methanol, ethanol, and isopropanol. In case of hydride reduction, the solvent includes, for example, diethyl ether, and tetrahydrofuran.

In order to adjust the reducing power or keep the stability of phenylenediamine compound obtained by reducing Compound a4, it is possible to use an additive such as hydrochloric acid and acetic acid.

The reaction time of the reduction reaction is generally 10 minutes to 24 hours, preferably 10 minutes to 5 hours.

The reaction temperature of the reduction reaction is generally 0° C. to boiling point of a solvent used herein, preferably 0° C. to 65° C.

As the cyclization condition used herein, formic acid or a formate equivalent may be added to the reaction solution after the reduction reaction, or formic acid or a formate equivalent may be added to the reduction reaction, i.e., without separating reduction reaction and cyclization reaction.

The formate equivalent includes orthoformates such as trimethyl orthoformate and triethyl orthoformate, more preferably trimethyl orthoformate and triethyl orthoformate. The catalyst used herein includes organic acid such as formic acid and acetic acid; Lewis acid such as ytterbium triflate; and inorganic acid such as hydrochloric acid and sulfuric acid; preferably formic acid.

The solvent used herein includes alcohol solvents such as methanol and ethanol; preferably methanol and ethanol. Or, formic acid or an orthoformate, etc. which is used as a catalyst or a formate equivalent may be also used as a solvent.

The reaction time of the cyclization is generally 10 minutes to 24 hours, preferably 5 hours to 16 hours.

The reaction temperature of the cyclization is generally 00° C. to boiling point of a solvent used herein, preferably 10° C. to 65° C.

Process 2:

The compound of formula (1) can be also prepared, for example, in a manner shown below.

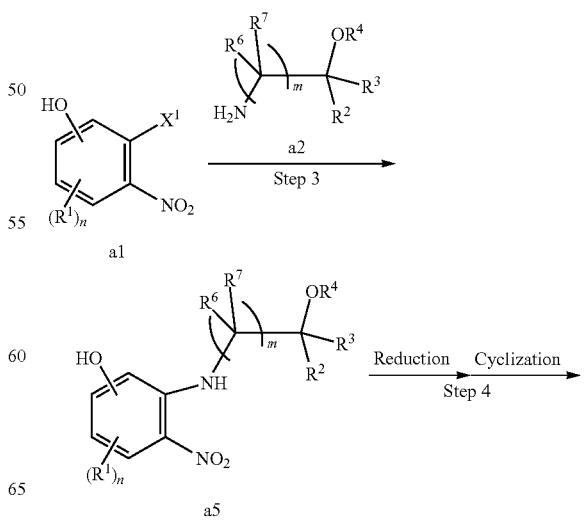

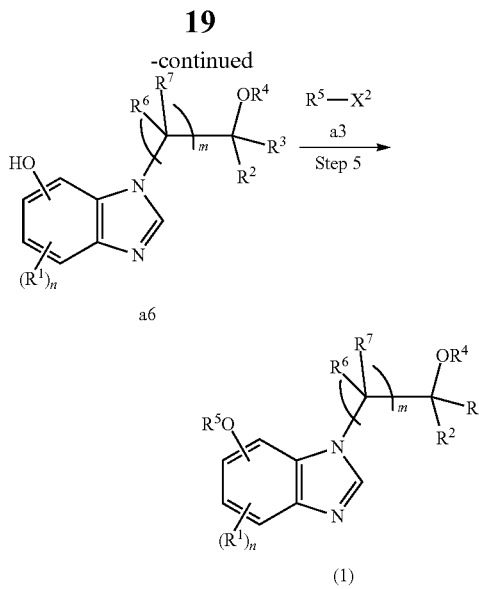

In the above scheme, $R^1$, $R^2$, $R^3$, $R^4$, $R^5$, $R^6$, $R^7$, m, and n are as defined in Item 1, and $X^1$ and $X^2$ are as defined in Item 2.

Step 3:
Compound a5 can be prepared from Compound a1 and Compound a2, according to the manner of Step 1.

Step 4:
Compound a6 can be prepared from Compound a5, according to the manner of Step 2.

Step 5:
The compound of formula (1) can be prepared from Compound a6 and Compound a3, according to the manner of Step 1.

EXAMPLES

The present invention is explained in more detail in the following by referring to Examples and Reference examples, however, the technical scope of the present invention should not be limited thereto.

Each compound was identified with a proton nuclear magnetic resonance spectrum ($^1$H-NMR spectrum), high-performance liquid chromatograph-mass spectrometer; LCMS, etc.

The measuring condition of high-performance liquid chromatography-mass spectrometer; LCMS is shown below, and the detected value of mass spectrography [MS (m/z)] is shown as M+H, and the retention time (min) is shown as T.

MS detector: ACUITY SQD
HPLC: ACUITY UPLC
Column: ACUITY BEH C18 1.7 μm, 2.1×50 mm
Mobile phase: A: 0.05% aqueous formic acid
B: acetonitrile
Gradient Program:

| 1 | 0.0-1.3 min | A:B = 90:10 => 1:99 |
| 2 | 1.3-1.5 min | A:B = 1:99 |
| 3 | 1.5-2.0 min | A:B = 90:10 |

Flow rate: 0.75 mL/min
Wave length: 254 nm
The HPLC area percentage of compounds was measured according to the following HPLC condition.
HPLC: Pump: Shimadzu 30A series,
Monitor: Shimadzu 20A series
Column: Kinetex 1.7 μm, C18 100A (100×2.1 mm)
Mobile phase: A: 0.05% trifluoroacetic acid/water
B: 0.05% trifluoroacetic acid/acetonitrile
Gradient Program:

| 0-1 min | A/B = 100:0 |
| 1-9 min | A/B = 100:0 => 10:90 |
| 9-13 min | A/B = 10:90 |

Flow rate: 0.3 mL/min
Wave length: 220 nm or 240 nm
Column temperature: 40° C.

In the following Examples and Reference examples, abbreviations shown below may be sometimes used to simplify the description of the present specification.

J: coupling constant, s: singlet, d: doublet, t: triplet, dd: double doublet, m: multiplet, brs: broad singlet.

Example Ex1

Preparation of 2-methyl-1-((2-nitro-5-((5-(trifluoromethyl)pyridin-2-yl)oxy)phenyl)amino)propan-2-ol

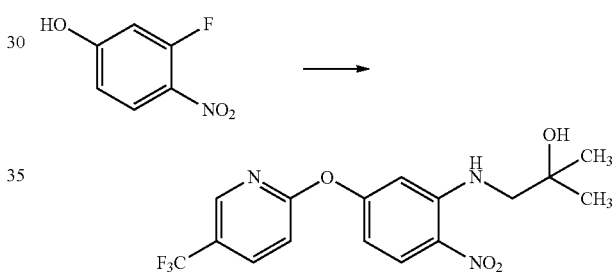

Synthetic Step 1-1

Under nitrogen atmosphere, a solution of 1-amino-2-methylpropan-2-ol (16.65 g) and sodium bicarbonate (6.68 g) in N-methylpyrrolidone (50 g) was warmed to 120° C., and a solution of 3-fluoro-4-nitrophenol (25 g) in N-methylpyrrolidone (75 g) was added thereto dropwise. The reaction mixture was stirred at 120° C. for 4 hours, and then cooled to room temperature. 2-Fluoro-5-(trifluoromethyl)pyridine (31.53 g) and potassium carbonate (37.39 g) were added to the reaction mixture, and the reaction mixture was stirred at 100° C. for 4 hours. The reaction mixture was cooled to 75° C., and then water (125 g) was added thereto to separate layers. The mixture was cooled to 50° C., and methanol (37.5 g) was added thereto. The mixture was cooled to 7° C., and stirred at 7° C. for 2 hours. Water (50 g) was added thereto dropwise, and the mixture was stirred for 2 more hours. The precipitated crystal was collected on a filter, washed with cooled 67% aqueous methanol (56 g) twice, and dried in vacuo to give the title compound (55.27 g, yield 93.5%).

HPLC area percentage: 99.7% (254 nm)
$^1$H-NMR (CDCl$_3$, 400 MHz) δ: 8.55-8.43 (m, 2H), 8.26 (d, J=9.4 Hz, 1H), 7.97 (dd, J=8.6, 2.4 Hz, 1H), 7.09 (d, J=8.6 Hz, 1H), 6.71 (d, J=2.4 Hz, 1H), 6.42 (dd, J=9.4, 2.4 Hz, 1H), 3.26 (d, J=5.5 Hz, 2H), 1.37 (s, 6H).

Synthetic Step 1-2

Under nitrogen atmosphere, a solution of 1-amino-2-methylpropan-2-ol (187.3 g) and diisopropylethylamine (600.1 g) in N-methylpyrrolidone (370 g) was warmed to 120° C., and a solution of 3-fluoro-4-nitrophenol (300 g) in N-methylpyrrolidone (900 g) was added thereto dropwise. The reaction mixture was stirred at 120° C. for 7 hours, and then cooled to room temperature. 2-Bromo-5-(trifluoromethyl)pyridine (561.0 g) and potassium carbonate (792.2 g) were added to the reaction mixture, and the reaction mixture was stirred at 100° C. for 15 hours. The reaction mixture was cooled to 75° C., and then water (1500 g) was added thereto to separate layers. The mixture was cooled to 25° C., and isopropanol (600 g) and water (1200 g) were added thereto. The mixture was cooled to 0° C. and left to stand at 0° C. for 1 hour. After a precipitated crystal was observed, water (1200 g) was added thereto, and the mixture was stirred for 20 hours. The precipitated crystal was collected on a filter, washed with cooled 33% aqueous isopropanol (900 g) twice, and dried in vacuo to give the title compound (592.2 g, yield 83.4%).

Example Ex2

Preparation of 2-methyl-1-(6-{[5-(trifluoromethyl)pyridin-2-yl]oxy}-1H-benzimidazol-1-yl)propan-2-ol

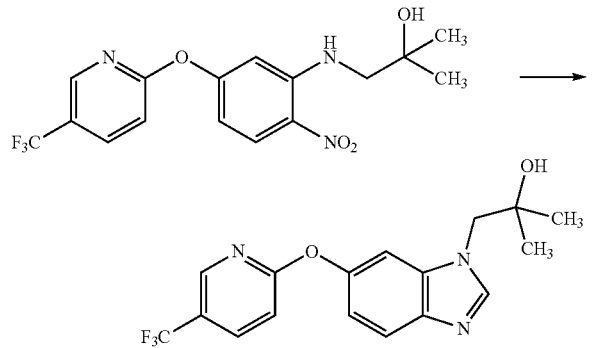

Synthetic Step 2-1

Under nitrogen atmosphere, to a solution of lithium bromide (18.95 g) in methanol (162 g) were added zinc powder (47.54 g) and methanol (108 g). And then, a solution of Example 1 compound (54 g) in methanol (270 g) and formic acid (40.16 g) were added to the reaction mixture dropwise keeping the temperature at 30° C. or lower. The mixture was stirred at 20° C. for 1 hour, and trimethyl orthoformate (77.16 g) and formic acid (20.08 g) were added thereto. The mixture was stirred at 20° C. for 18 hours. The reaction solution was warmed to 45° C. and stirred for 1 hour, and then the zinc residue was removed by filtration and washed with hot methanol (162 g) twice. The filtrate was concentrated in vacuo, and isopropyl acetate (540 g) was added to the residue. The solution was concentrated in vacuo. Isopropyl acetate (627 g) and water (540 g) were added to the concentrated solution to separate layers at 75° C. The organic layer was washed at 75° C. with 23% aqueous trisodium citrate (702 g), 7% aqueous sodium bicarbonate (581 g), and then water (540 g), and concentrated in vacuo. The concentrated solution was cooled to room temperature, and left to stand at room temperature for 1 hour. The precipitated crystal was collected on a filter, washed with isopropyl acetate (108 g), and dried in vacuo to give the title compound as a crude crystal (48.38 g, yield 94.7%). The obtained crude crystal (47 g) was recrystallized with isopropanol to give the title compound (44.33 g, yield after recrystallization 94.3%) HPLC area percentage: 99.9% (220 nm)

$^1$H-NMR (CD$_3$OD, 400 MHz) δ: 8.44-8.40 (m, 1H), 8.19 (s, 1H), 8.08 (dd, J=8.8, 2.2 Hz, 1H), 7.71 (d, J=8.7 Hz, 1H), 7.50 (d, J=2.1 Hz, 1H), 7.12 (d, J=8.8 Hz, 1H), 7.08 (dd, J=8.7, 2.2 Hz, 1H), 4.20 (s, 2H), 1.21 (s, 6H).

Synthetic Step 2-2

Under nitrogen atmosphere, to a solution of Example 1 compound (100 mg) in ethanol (0.5 g) were added 3% platinum sulfide on carbon (wetted) (10 mg) and concentrated hydrochloric acid (136 mg). The gas in the reaction vessel was replaced by hydrogen, and then the reaction mixture was stirred at room temperature for 7 hours. The gas in the reaction vessel was replaced by nitrogen, and then trimethyl orthoformate (764 μL) was added thereto. The mixture was stirred at room temperature for 3 hours and at 50° C. for 1 hour, and then filtrated with Celite and washed with ethanol. The filtrate was concentrated in vacuo. Isopropyl acetate and aqueous sodium bicarbonate were added to the concentrated solution to separate layers. The organic layer was washed with brine to give the title compound as a crude crystal (83.5 mg).

Synthetic Step 2-3

To a solution of Example 1 compound (0.50 g) in methanol (6.7 mL) were added trimethyl orthoformate (3.7 mL), formic acid (0.52 mL) and zinc powder (0.44 g), and the reaction mixture was stirred at 70° C. for 2 hour. The reaction mixture was filtrated with Celite and the filtrate was concentrated in vacuo. The obtained residue was dissolved in ethyl acetate, washed with aqueous Rochelle salt and brine, and dried over anhydrous sodium sulfate. The solution was concentrated to give a crude crystal. The crude crystal was recrystallized with hexane/ethyl acetate (1/5) to give the title compound (0.33 g).

Reference Example RE1

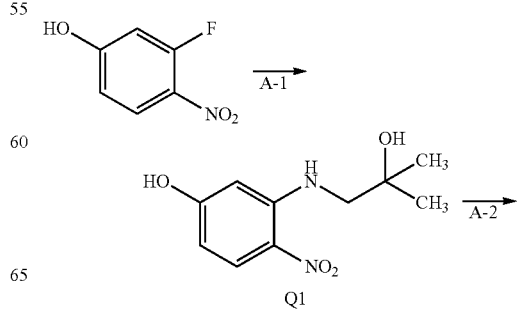

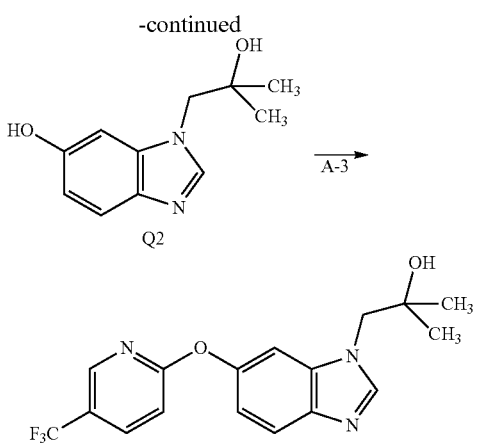

Preparation of 3-[(2-hydroxy-2-methylpropyl)amino]-4-nitrophenol (Compound Q1)

Under nitrogen atmosphere, a solution of 1-amino-2-methylpropan-2-ol (15.6 g) and diisopropylethylamine (30.9 g) in N-methylpyrrolidone (25 g) was warmed to 120° C., and a solution of 3-fluoro-4-nitrophenol (25 g) in N-methylpyrrolidone (91 g) was added thereto dropwise. The reaction mixture was stirred at 120° C. for 7 hours, and cooled to room temperature. The reaction solution was added to 1 mol/L hydrochloric acid (1041 g) dropwise, and the mixture was stirred at room temperature for 1 hour. The precipitated crystal was collected on a filter, washed with water (100 g) three times, and dried in vacuo to give the title compound (29.3 g, yield 81.4%).

HPLC area percentage: 99.8% (254 nm)
$^1$H-NMR (DMSO-$d_6$, 400 MHz) δ: 10.75 (s, 1H), 8.47 (t, J=5.0 Hz, 1H), 7.97 (d, J=9.4 Hz, 1H), 6.20 (d, J=2.4 Hz, 1H), 6.17 (dd, J=9.4, 2.4 Hz, 1H), 4.82 (s, 1H), 3.13 (d, J=5.0 Hz, 2H), 1.20 (s, 6H).

Preparation of 1-(2-hydroxy-2-methylpropyl)-1H-benzimidazol-6-ol (Compound Q2)

Under nitrogen atmosphere, to a solution of Compound Q1 (5 g) in ethanol (50 g) were added lithium bromide (1.9 g), zinc powder (7.2 g), and trimethyl orthoformate (58.6 g). Then, formic acid (10.2 g) was added to the reaction mixture dropwise at room temperature, and the reaction mixture was stirred for 3 hours. The reaction mixture was filtrated with Celite, and the filtrate was concentrated. The obtained residue was charged on amino silica gel (50 g), and eluted with chloroform/methanol (1 L/250 mL). The filtrate was concentrated in vacuo, and the precipitated solid was recrystallized with isopropanol (25 g) to give the title compound (3.5 g, yield 76.3%).

HPLC area percentage: 100.0% (254 nm)
$^1$H-NMR (DMSO-$d_6$, 400 MHz) δ: 9.20 (br s, 1H), 7.88 (s, 1H), 7.38 (d, J=8.6 Hz, 1H), 6.91 (d, J=2.2 Hz, 1H), 6.66 (dd, J=8.6, 2.2 Hz, 1H), 4.74 (br s, 1H), 4.00 (s, 2H), 1.09 (s, 6H).

Preparation of 2-methyl-1-(6-{[5-(trifluoromethyl)pyridin-2-yl]oxy}-1H-benzimidazol-1-yl)propan-2-ol (Reference Example RE-3)

Under argon atmosphere, to a solution of Compound Q2 (1.10 kg) in N,N-dimethylformamide (31.4 kg) were added cesium carbonate (2.61 kg) and 2-fluoro-5-(trifluoromethyl)pyridine (1.14 kg). The reaction mixture was warmed to 60° C. and stirred for 25 hours. The reaction solution was cooled to room temperature. Water (16.5 kg), ethyl acetate (7.93 kg), and toluene (6.68 kg) were added to the reaction solution to separate layers. To the aqueous layer was added salt (2.2 kg), and the mixture was stirred. Ethyl acetate (1.98 kg) and toluene (3.81 kg) were added thereto, and the organic layer was collected. The recovery procedure was repeated twice. The combined organic layer was concentrated in vacuo to give the title compound as a crude crystal (1.11 kg, yield 59.5%). The obtained crude crystal was recrystallized with ethyl acetate (20.0 kg) and hexane (3.77 kg) to give the title compound (0.97 kg, yield after recrystallization 87.3%).

HPLC area percentage: 99.7% (254 nm)

Examples Ex3-6

According to the process of the above-mentioned Example Ex1, the following compounds of Examples Ex3-6 were prepared with each corresponding starting material.

| Example | $R^A$ | [M + H]$^+$ | T (min) |
|---|---|---|---|
| Ex3 | H₃C—C(OH)(CH₃)—CH₂— | 386 | 1.028 |
| Ex4 | H₃C—C(OH)(CH₃)— | 372 | 1.117 |
| Ex5 | H₃C(,,,)—CH(CH₃)—C(OH)(CH₃)— | 386 | 1.023 |
| Ex6 | H₃C—CH(CH₃)—C(OH)(CH₃)— | 386 | 1.019 |

Examples Ex7-10

According to the process of the above-mentioned Example Ex2, the following compounds of Examples Ex7-10 were prepared with each corresponding starting material.

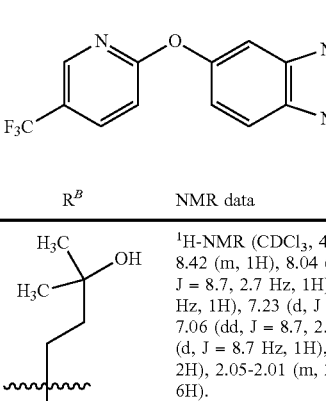

| Example | $R^B$ | NMR data |
|---|---|---|
| Ex7 | 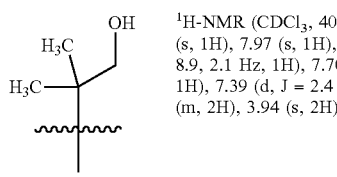 | $^1$H-NMR (CDCl$_3$, 400 MHz) δ: 8.42-8.42 (m, 1H), 8.04 (s, 1H), 7.89 (dd, J = 8.7, 2.7 Hz, 1H), 7.82 (d, J = 8.7 Hz, 1H), 7.23 (d, J = 2.3 Hz, 1H), 7.06 (dd, J = 8.7, 2.3 Hz, 1H), 7.02 (d, J = 8.7 Hz, 1H), 4.34-4.30 (m, 2H), 2.05-2.01 (m, 2H), 1.31 (s, 6H). |
| Ex8 | 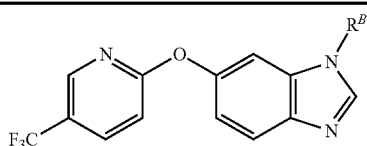 | $^1$H-NMR (CDCl$_3$, 400 MHz) δ: 8.40 (s, 1H), 7.97 (s, 1H), 7.88 (dd, J = 8.9, 2.1 Hz, 1H), 7.70 (d, J = 8.5 Hz, 1H), 7.39 (d, J = 2.4 Hz, 1H), 7.00 (m, 2H), 3.94 (s, 2H), 1.73 (s, 6H). |

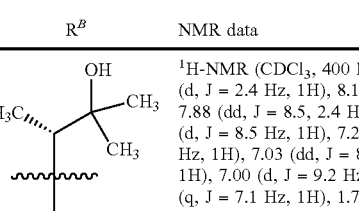

| Example | $R^B$ | NMR data |
|---|---|---|
| Ex9 | 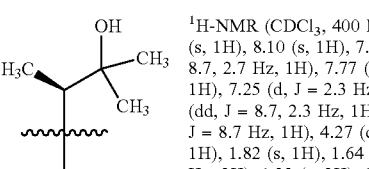 | $^1$H-NMR (CDCl$_3$, 400 MHz) δ: 8.41 (d, J = 2.4 Hz, 1H), 8.11 (s, 1H), 7.88 (dd, J = 8.5, 2.4 Hz, 1H), 7.78 (d, J = 8.5 Hz, 1H), 7.25 (d, J = 2.4 Hz, 1H), 7.03 (dd, J = 8.9, 2.1 Hz, 1H), 7.00 (d, J = 9.2 Hz, 1H), 4.27 (q, J = 7.1 Hz, 1H), 1.73 (s, 1H), 1.64 (d, J = 7.3 Hz, 3H), 1.33 (s, 3H), 1.15 (s, 3H). |
| Ex10 | 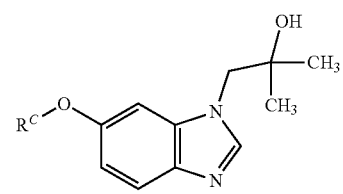 | $^1$H-NMR (CDCl$_3$, 400 MHz) δ: 8.41 (s, 1H), 8.10 (s, 1H), 7.88 (dd, J = 8.7, 2.7 Hz, 1H), 7.77 (d, J = 8.7 Hz, 1H), 7.25 (d, J = 2.3 Hz, 1H), 7.02 (dd, J = 8.7, 2.3 Hz, 1H), 6.99 (d, J = 8.7 Hz, 1H), 4.27 (q, J = 7.2 Hz, 1H), 1.82 (s, 1H), 1.64 (d, J = 7.3 Hz, 3H), 1.33 (s, 3H), 1.14 (s, 3H). |

Reference Example RE2-16

According to the process of the above-mentioned Reference example RE1, the following compounds of Reference examples RE2-16 were prepared with each corresponding starting material.

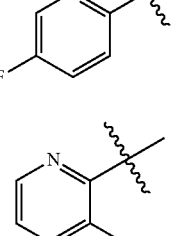

| Reference example | $R^C$ | NMR data |
|---|---|---|
| RE2 | 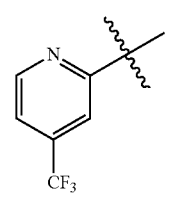 | $^1$H-NMR (CDCl$_3$, 400 MHz) δ: 7.92 (d, J = 3.1 Hz, 1H), 7.89 (s, 1H), 7.65 (d, J = 9.2 Hz, 1H), 7.38-7.33 (m, 1H), 7.17 (d, J = 2.4 Hz, 1H), 6.94 (dd, J = 8.9, 2.1 Hz, 1H), 6.82 (dd, J = 9.2, 3.7 Hz, 1H), 4.00 (s, 2H), 1.22 (s, 6H). |
| RE3 | | $^1$H-NMR (CDCl$_3$, 400 MHz) δ: 8.24 (dd, J = 4.9, 1.8 Hz, 1H), 7.99-7.97 (m, 2H), 7.79 (d, J = 8.5 Hz, 1H), 7.29 (d, J = 1.8 Hz, 1H), 7.08-7.04 (m, 2H), 4.08 (s, 2H), 1.65 (s, 1H), 1.28 (s, 6H). |
| RE4 | | $^1$H-NMR (CDCl$_3$, 400 MHz) δ: 8.29 (d, J = 5.5 Hz, 1H), 7.97 (s, 1H), 7.79 (d, J = 8.9 Hz, 1H), 7.26 (d, J = 2.1 Hz, 1H), 7.17 (d, J = 5.5 Hz, 1H), 7.13 (s, 1H), 7.04 (dd, J = 8.9, 2.1 Hz, 1H), 4.07 (s, 2H), 1.75 (s, 1H), 1.28 (s, 6H). |

-continued

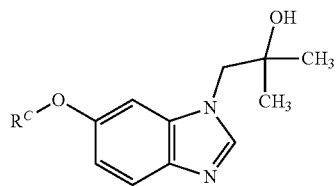

| Reference example | $R^C$ | NMR data |
|---|---|---|
| RE5 | (6-trifluoromethylpyridin-2-yl)methyl | $^1$H-NMR (CDCl$_3$, 400 MHz) δ: 7.98 (s, 1H), 7.82-7.75 (m, 2H), 7.36-7.35 (m, 2H), 7.05-7.03 (m, 2H), 4.07 (s, 2H), 1.69 (s, 1H), 1.28 (s, 6H). |
| RE6 | (5-difluoromethylpyridin-2-yl)methyl | $^1$H-NMR (CDCl$_3$, 400 MHz) δ: 8.24 (s, 1H), 7.95 (s, 1H), 7.82 (d, J = 9.2 Hz, 1H), 7.77 (d, J = 8.5 Hz, 1H), 7.26 (d, J = 1.8 Hz, 1H), 7.04-6.97 (m, 2H), 6.63 (t, J = 55.8 Hz, 1H), 4.07 (s, 2H), 1.95 (s, 1H), 1.28 (s, 6H). |
| RE7 | (5-chloropyridin-2-yl)methyl | $^1$H-NMR (CDCl$_3$, 400 MHz) δ: 8.08 (d, J = 2.4 Hz, 1H), 7.95 (s, 1H), 7.76 (d, J = 8.5 Hz, 1H), 7.63-7.60 (m, 1H), 7.23 (d, J = 1.8 Hz, 1H), 7.02 (dd, J = 9.2, 1.8 Hz, 1H), 6.86 (d, J = 8.5 Hz, 1H), 4.06 (s, 2H), 1.81 (s, 1H), 1.28 (s, 6H). |
| RE8 | (6-trifluoromethylpyridazin-3-yl)methyl | $^1$H-NMR (CDCl$_3$, 400 MHz) δ: 7.98 (s, 1H), 7.82 (d, J = 8.5 Hz, 1H), 7.78 (d, J = 9.8 Hz, 1H), 7.39 (d, J = 2.1 Hz, 1H), 7.30 (d, J = 9.8 Hz, 1H), 7.10 (dd, J = 8.5, 2.1 Hz, 1H), 4.08 (s, 2H), 1.63 (s, 1H), 1.28 (s, 6H). |
| RE9 | (5-trifluoromethylpyrazin-2-yl)methyl | $^1$H-NMR (CDCl$_3$, 400 MHz) δ: 8.49 (s, 1H), 8.40 (s, 1H), 7.99 (s, 1H), 7.82 (d, J = 8.9 Hz, 1H), 7.30 (d, J = 2.1 Hz, 1H), 7.06 (dd, J = 8.9, 2.1 Hz, 1H), 4.08 (s, 2H), 1.66 (s, 1H), 1.29 (s, 6H). |
| RE10 | (6-chloropyridazin-3-yl)methyl | $^1$H-NMR (CDCl$_3$, 400 MHz) δ: 7.93 (s, 1H), 7.76 (d, J = 8.5 Hz, 1H), 7.47 (d, J = 9.2 Hz, 1H), 7.35 (d, J = 2.4 Hz, 1H), 7.15 (d, J = 9.2 Hz, 1H), 7.06 (dd, J = 8.5, 2.4 Hz, 1H), 4.03 (s, 2H), 2.05 (s, 1H), 1.26 (s, 6H). |
| RE11 | (5-chloro-3-fluoropyridin-2-yl)methyl | $^1$H-NMR (CDCl$_3$, 400 MHz) δ: 7.95 (s, 1H), 7.83-7.83 (m, 1H), 7.77-7.75 (m, 1H), 7.51-7.49 (m, 1H), 7.27-7.27 (m, 1H), 7.06-7.03 (m, 1H), 4.07 (s, 2H), 1.82 (s, 1H), 1.28 (s, 6H). |
| RE12 | (3-fluoro-5-trifluoromethylpyridin-2-yl)methyl | $^1$H-NMR (CDCl$_3$, 400 MHz) δ: 8.13 (d, J = 2.4 Hz, 1H), 7.98 (s, 1H), 7.80 (d, J = 8.9 Hz, 1H), 7.68 (dd, J = 9.5, 2.1 Hz, 1H), 7.31 (d, J = 2.4 Hz, 1H), 7.07 (dd, J = 8.9, 2.1 Hz, 1H), 4.08 (s, 2H), 1.68 (s, 1H), 1.29 (s, 6H). |

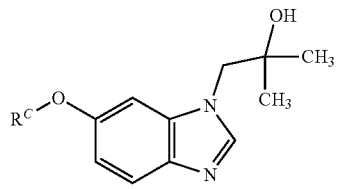

| Reference example | R^C | NMR data |
|---|---|---|
| RE13 | 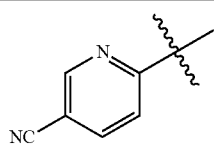 [SMILES: *c1ccc(C#N)cn1] | ¹H-NMR (CDCl₃, 400 MHz) δ: 8.43-8.42 (m, 1H), 7.97 (s, 1H), 7.90 (dd, J = 8.7, 2.3 Hz, 1H), 7.79 (d, J = 8.7 Hz, 1H), 7.26 (d, J = 2.3 Hz, 1H), 7.03-7.00 (m, 2H), 4.07 (s, 2H), 1.81 (s, 1H), 1.28 (s, 6H). |
| RE14 | 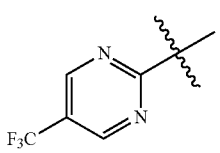 | ¹H-NMR (CDCl₃, 400 MHz) δ: 8.77 (s, 2H), 7.99 (s, 1H), 7.81 (d, J = 8.5 Hz, 1H), 7.31 (d, J = 2.4 Hz, 1H), 7.08 (dd, J = 8.5, 2.4 Hz, 1H), 4.08 (s, 2H), 1.71 (s, 1H), 1.29 (s, 6H). |
| RE15 | 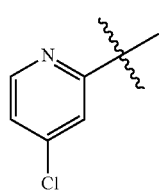 [SMILES: *c1cc(Cl)ccn1] | ¹H-NMR (CDCl₃, 400 MHz) δ: 8.19 (d, J = 5.5 Hz, 1H), 8.01 (s, 1H), 7.80 (d, J = 8.5 Hz, 1H), 7.19 (d, J = 1.8 Hz, 1H), 7.00-6.98 (m, 1H), 6.78-6.77 (m, 2H), 4.08 (s, 2H), 1.70 (s, 1H), 1.28 (s, 6H). |
| RE16 | 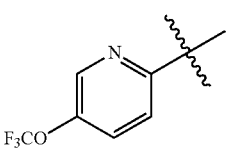 [SMILES: *c1ccc(OC(F)(F)F)cn1] | ¹H-NMR (CDCl₃, 400 MHz) δ: 8.07 (d, J = 3.1 Hz, 1H), 7.96 (s, 1H), 7.79 (d, J = 8.5 Hz, 1H), 7.57-7.53 (m, 1H), 7.25 (d, J = 2.4 Hz, 1H), 7.04 (dd, J = 8.5, 2.4 Hz, 1H), 6.94 (d, J = 8.5 Hz, 1H), 4.07 (s, 2H), 1.61 (s, 1H), 1.28 (s, 6H). |

According to the processes of Examples Ex1 and Ex2, and Reference example RE1, the following compounds can be prepared.

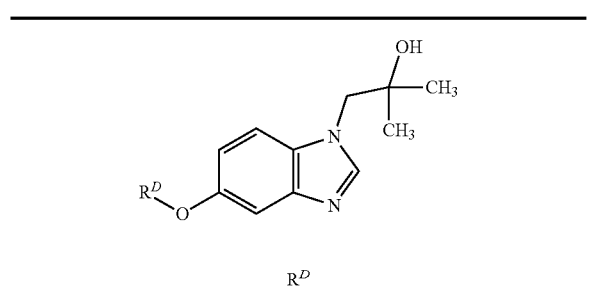

R^D

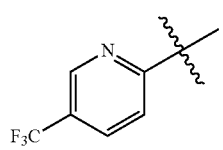

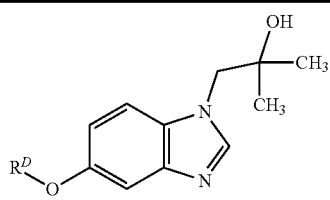

R^D

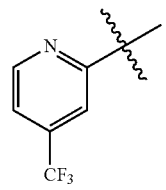 [SMILES: *c1cc(C(F)(F)F)ccn1]

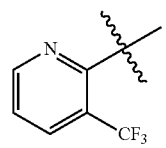

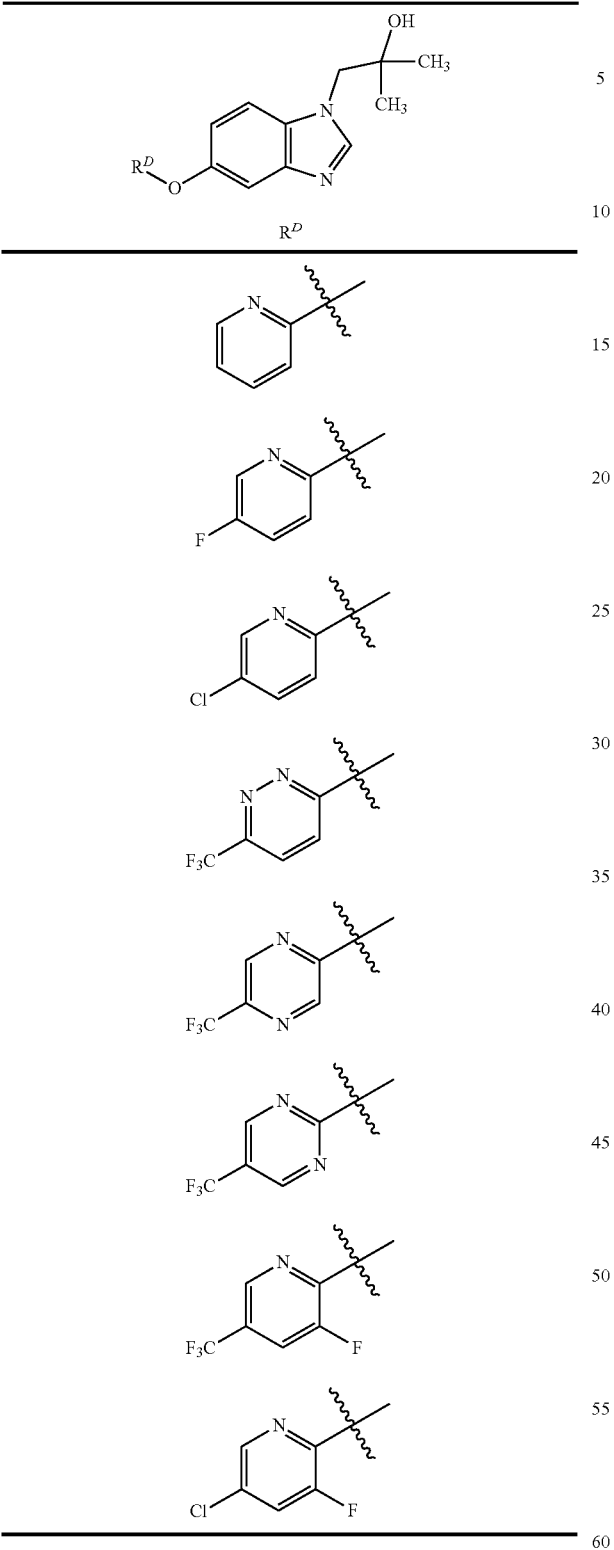

INDUSTRIAL APPLICABILITY

The present invention can provide a process of preparing a benzimidazole derivative, which can prepare the desired product in short reaction processes without a protection/deprotection process.

The invention claimed is:
1. A process for preparing a compound of formula (1):

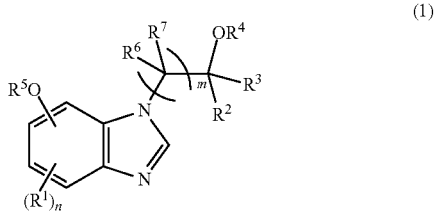

or a pharmaceutically acceptable salt thereof, wherein
each $R^1$ is independently halogen, cyano, $C_{1-6}$ alkyl, or $C_{1-6}$ alkoxy, wherein the alkyl and the alkoxy may be optionally substituted with 1 to 5 independently selected halogen atoms;
n is 0, 1, 2, or 3;
$R^2$ and $R^3$ are independently hydrogen; $C_{1-6}$ alkyl which may be optionally substituted with 1 to 5 substituents independently selected from the group consisting of cyano, halogen, and hydroxy; or $C_{3-10}$ cycloalkyl;
$R^4$ is hydrogen; $C_{1-6}$ alkyl which may be optionally substituted with 1 to 5 substituents independently selected from the group consisting of cyano, halogen, and hydroxy; or $C_{3-10}$ cycloalkyl;
$R^5$ is $C_{6-10}$ aryl or 5- to 12-membered heteroaryl, wherein the aryl and the heteroaryl may be optionally substituted with 1 to 5 substituents independently selected from the group consisting of halogen; $C_{1-4}$ alkyl which may be optionally substituted with 1 to 5 independently selected halogen atoms; and $C_{1-4}$ alkoxy which may be optionally substituted with 1 to 5 independently selected halogen atoms;
m is 1, 2, or 3; and
$R^6$ and $R^7$ are each independently selected from the group consisting of hydrogen, deuterium, hydroxy, $C_{1-4}$ alkyl, $C_{1-4}$ alkoxy, $C_{3-7}$ cycloalkyl, and $C_{3-7}$ cycloalkoxy, wherein the $C_{1-4}$ alkyl, $C_{1-4}$ alkoxy, $C_{3-7}$ cycloalkyl, and $C_{3-7}$ cycloalkoxy may be optionally substituted with 1 to 5 substituents independently selected from the group consisting of halogen and hydroxy,
comprising reducing a compound of formula (2):

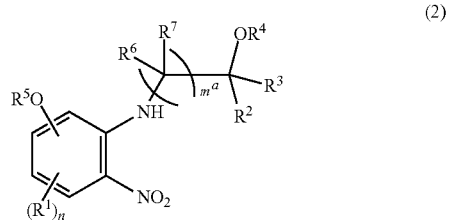

wherein the reduction is carried out with (i) an oxide-layer remover; and (ii) a reducing metal, a reducing metal salt, or a mixture of a reducing metal and a reducing metal salt; and
wherein the oxide-layer remover is lithium bromide, lithium chloride, or chlorotrimethylsilane; and
cyclizing the reduced product with a formate equivalent.

2. The process of claim 1, further comprising a step of preparing the compound of formula (2) which comprises reacting a compound of formula (3):

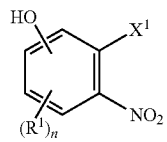
(3)

wherein $X^1$ is hydroxy, halogen, alkylsulfonyloxy, or arylsulfonyloxy,
with a compound of (4):

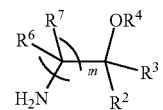
(4)

and then
with $R^5$—$X^2$, wherein $X^2$ is halogen.

3. A process for preparing a compound of formula (1):

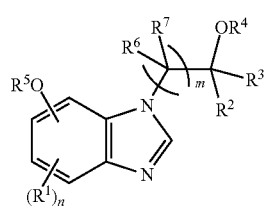
(1)

or a pharmaceutically acceptable salt thereof, wherein
each $R^1$ is independently halogen, cyano, $C_{1-6}$ alkyl, or $C_{1-6}$ alkoxy, wherein the $C_{1-6}$ alkyl and the $C_{1-6}$ alkoxy may be optionally substituted with 1 to 5 independently selected halogen atoms;
n is 0, 1, 2, or 3;
$R^2$ and $R^3$ are each independently hydrogen; $C_{1-6}$ alkyl which may be optionally substituted with 1 to 5 substituents independently selected from the group consisting of cyano, halogen, and hydroxy; or $C_{3-10}$ cycloalkyl;
$R^4$ is hydrogen; $C_{1-6}$ alkyl which may be optionally substituted with 1 to 5 substituents independently selected from the group consisting of cyano, halogen, and hydroxy; or $C_{3-10}$ cycloalkyl;
$R^5$ is $C_{6-10}$ aryl or 5- to 12-membered heteroaryl, wherein the aryl and the heteroaryl may be optionally substituted with 1 to 5 substituents independently selected from the group consisting of halogen; $C_{1-4}$ alkyl which may be optionally substituted with 1 to 5 independently selected halogen atoms; and $C_{1-4}$ alkoxy which may be optionally substituted with 1 to 5 independently selected halogen atoms;
m is 1, 2, or 3; and
$R^6$ and $R^7$ are each independently selected from the group consisting of hydrogen, deuterium, hydroxy, $C_{1-4}$ alkyl, $C_{1-4}$ alkoxy, $C_{3-7}$ cycloalkyl, and $C_{3-7}$ cycloalkoxy, wherein the $C_{1-4}$ alkyl, $C_{1-4}$ alkoxy, $C_{3-7}$ cycloalkyl, and $C_{3-7}$ cycloalkoxy may be optionally substituted with 1 to 5 substituents independently selected from the group consisting of halogen and hydroxy, comprising reacting a compound of formula (3):

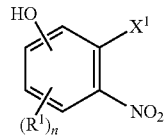
(3)

wherein $X^1$ is hydroxy, halogen, alkylsulfonyloxy, or arylsulfonyloxy,
with a compound of (4):

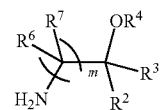
(4)

and then
with $R^5$—$X^2$ wherein $X^2$ is halogen, to prepare a compound of formula (2):

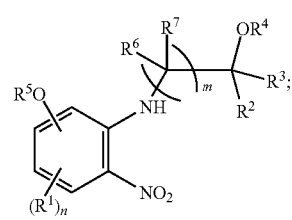
(2)

reducing the compound of formula (2), wherein the reduction is carried out (i) with an oxide-layer remover; and (ii) a reducing metal, a reducing metal salt, or a mixture of a reducing metal and a reducing metal salt and wherein the oxide-layer remover is lithium bromide, lithium chloride, or chlorotrimethylsilane; and cyclizing the reduced product with a formate equivalent to prepare the compound of formula (1).

4. The process of claim 1, wherein the compound of formula (1) is a compound of formula (1'):

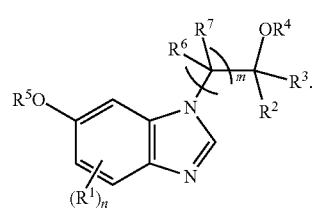
(1')

5. The process of claim 2, wherein
n is 0;
$R^2$ and $R^3$ are each independently hydrogen or $C_{1-6}$ alkyl;
$R^4$ is hydrogen or $C_{1-6}$ alkyl;

R⁵ is phenyl or 5- or 6-membered heteroaryl, wherein the phenyl and the heteroaryl may be optionally substituted with 1 to 5 substituents independently selected from the group consisting of halogen; $C_{1-4}$ alkyl which may be optionally substituted with 1 to 5 independently selected halogen atoms; and $C_{1-4}$ alkoxy which may be optionally substituted with 1 to 5 independently selected halogen atoms;

m is 1;

R⁶ and R⁷ are independently hydrogen, deuterium, or $C_{1-4}$ alkyl;

X¹ is halogen; and

X² is fluorine or bromine.

6. The process of claim 1, wherein
R⁵ is pyridyl, pyrazinyl, pyrimidinyl, or pyridazinyl, wherein the pyridyl, the pyrazinyl, the pyrimidinyl, and the pyridazinyl may be optionally substituted with 1 to 5 substituents independently selected from the group consisting of halogen; $C_{1-4}$ alkyl which may be optionally substituted with 1 to 5 independently selected halogen atoms; and $C_{1-4}$ alkoxy which may be optionally substituted with 1 to 5 independently selected halogen atoms.

7. The process of claim 1, wherein the reduction reaction is carried out with a reducing metal.

8. The process of claim 7, wherein the reducing metal is zinc or iron.

9. The process of claim 1, wherein the reduction reaction is carried out with a catalyst for catalytic reduction under hydrogen atmosphere.

10. The process of claim 9, wherein the catalyst for catalytic reduction is palladium-carbon or platinum sulfide on carbon.

11. The process of claim 1, wherein the reduction reaction is carried out in the presence of an acid.

12. The process of claim 1, wherein the formate equivalent is one or more selected from the group consisting of orthoformate triester, formic acid ester, and formate.

13. The process of claim 12, wherein the formate equivalent is orthoformate triester.

14. The process of claim 1, wherein the reduction and the cyclization are carried out in a one-pot reaction.

15. The process of claim 1, wherein in the reduction and the cyclization, the nitro is reduced, followed by adding an acid and a formate equivalent to make cyclization.

16. The process of claim 1, wherein in the reduction and the cyclization, the nitro is reduced in the presence of an acid and a formate equivalent to make cyclization in the reaction system after the reduction.

17. The process of claim 11, wherein the acid is formic acid.

* * * * *